(12) United States Patent
He et al.

(10) Patent No.: US 12,306,142 B2
(45) Date of Patent: May 20, 2025

(54) CLAMP OF ELASTIC BOX OF STIFF TRUE-TRIAXIAL TESTING SYSTEM AND DISPLACEMENT MONITORING METHOD FOR CUBOID SPECIMENS

(71) Applicant: Northeastern University, Heping District (CN)

(72) Inventors: Benguo He, Shenyang (CN); Xiating Feng, Shenyang (CN); Rongli Zhen, Shenyang (CN); Xiwei Zhang, Shenyang (CN); Chengxiang Yang, Shenyang (CN); Mian Tian, Shenyang (CN); Hongpu Li, Shenyang (CN); Hongyuan Fu, Shenyang (CN)

(73) Assignee: NORTHEASTERN UNIVERSITY, Shenyang (CN)

( * ) Notice: Subject to any disclaimer, the term of this patent is extended or adjusted under 35 U.S.C. 154(b) by 323 days.

(21) Appl. No.: 18/024,200

(22) PCT Filed: Jan. 5, 2022

(86) PCT No.: PCT/CN2022/070315
§ 371 (c)(1),
(2) Date: Mar. 1, 2023

(87) PCT Pub. No.: WO2022/096034
PCT Pub. Date: May 12, 2022

(65) Prior Publication Data
US 2023/0273103 A1    Aug. 31, 2023

(30) Foreign Application Priority Data
Nov. 6, 2020    (CN) .......................... 202011230622.5

(51) Int. Cl.
*G01N 3/04*    (2006.01)
*G01N 3/06*    (2006.01)
(Continued)

(52) U.S. Cl.
CPC ............... *G01N 3/04* (2013.01); *G01N 3/066* (2013.01); *G01N 3/08* (2013.01); *G01N 33/24* (2013.01);
(Continued)

(58) Field of Classification Search
CPC ............ G01N 3/08; G01N 3/04; G01N 3/066; G01N 2203/0067; G01N 2203/0256;
(Continued)

(56) References Cited

U.S. PATENT DOCUMENTS

2015/0168282 A1    6/2015    He et al.
2019/0226958 A1*   7/2019    Ju ........................... G01N 3/12

FOREIGN PATENT DOCUMENTS

CN    105865907 A    8/2016
CN    106290787 A    1/2017
(Continued)

*Primary Examiner* — Jonathan M Dunlap
(74) *Attorney, Agent, or Firm* — MUNCY, GEISSLER, OLDS & LOWE, P.C.

(57) ABSTRACT

Provided is a clamp of elastic box of stiff true-triaxial testing system and a displacement monitoring method for cuboid specimens. The clamp includes six pressing plates and eight plate springs, which form an elastic pressure box. One surface of the elastic pressure box can be disassembled, which simplifies the steps of rock sample mounting, and saving the mounting time. The springs connected with the pressing plates ensures the stability of the clamp but cannot affect the stress state of other surfaces of the rock sample during the test of the rock sample, thereby ensuring test accuracy. The invention further provides a displacement monitoring method for the rock sample by using the elastic box clamp. Six displacement sensors are mounted on the elastic box clamp, and the displacement of the rock sample can be monitored in real time.

9 Claims, 8 Drawing Sheets

(51) Int. Cl.
*G01N 3/08* (2006.01)
*G01N 33/24* (2006.01)

(52) U.S. Cl.
CPC ............... *G01N 2203/0067* (2013.01); *G01N 2203/0256* (2013.01); *G01N 2203/0447* (2013.01)

(58) Field of Classification Search
CPC ... G01N 2203/0447; G01N 2203/0019; G01N 2203/0682; G01N 2203/0423; G01N 33/24; G01B 7/02
See application file for complete search history.

(56) References Cited

FOREIGN PATENT DOCUMENTS

| | | | |
|---|---|---|---|
| CN | 106596281 A | | 4/2017 |
| CN | 109323920 A | | 2/2019 |
| CN | 110044689 A | | 7/2019 |
| CN | 112414838 A | | 2/2021 |
| CN | 116124672 A | * | 5/2023 |
| CN | 118961387 A | * | 11/2024 |

\* cited by examiner

CLAMP OF ELASTIC BOX OF STIFF TRUE-TRIAXIAL TESTING SYSTEM AND DISPLACEMENT MONITORING METHOD FOR CUBOID SPECIMENS

BACKGROUND OF THE INVENTION

1. Field of the Invention

The invention relates to the technical field of an indoor testing system of rock mechanics, to a clamp of elastic box of stiff true-triaxial testing system and a displacement monitoring method for cuboid specimens.

2. The Prior Arts

Traffic, water conservancy and hydropower, metal mines, physical underground laboratories, national defence, oil and gas, nuclear waste underground storage and other projects constantly develop towards deep underground, and the overburden and in-situ stress are increasing. Nowadays, development and utilization of underground space are inevitable requirement for the development of urbanization; discovering resources towards the deep is the strategic choice to achieve sustainable development; and the specific requirements of deep underground burial of high radioactive waste, grasping the changes of the deep state of the earth, early warning of natural disasters, and the like have promoted our world to issue the order of "Marching towards the deep of the earth". However, along with underground excavation, the stress in the periphery of opening would redistribute, so that the surrounding rocks are unstable and even generate rock burst, seriously affecting the construction safety. Therefore, the use of indoor physical tests to study a rock burst mechanism and influencing factors is of great importance to engineering design and construction safety.

Many researchers have performed a lot of research campaigns, focusing on uniaxial rock burst test, biaxial rock burst test, conventional triaxial rock burst test, and true-triaxial rock burst test to single face unloading true-triaxial rock burst test. According to different test loading methods and test instruments, there will be different requirements for rock sample clamps. At present, a traditional clamp could be divided into a stiff-soft composite loading clamp and a stiff loading clamp, respectively. The stiff loading surface of a stiff-soft composite loading clamp test piece is wrapped with a stiff cushion block, and the soft loading surface needs to be coated with a sealant. The operation process is complicated, and the uniformity of the sealant will also generate a certain impact on test results. A testing machine cannot meet the requirements of hexahedral stiff loading, cannot realize rapid unloading of one-direction or two-direction principal stress, and cannot realize the rock burst test research either. The stiff clamp is generally a sliding clamp, and its two sliding blocks restrict each other. If the stress state of one surface is changed, the adjacent surfaces are also affected. The requirements for true-triaxial test of hard rocks and relevant tests requiring true-triaxial single face unloading conditions cannot be met. Therefore, it is necessary to invent a sample clamp for a hexahedral stiff loading testing machine under different conditions.

SUMMARY OF THE INVENTION

In view of the defects existing in the existing technology, the invention provides a clamp of elastic box of stiff true-triaxial testing system and displacement monitoring method for cuboid specimens. The clamp can fully meet the mounting requirements for the sample by a stiff true-triaxial testing machine, and a traditional two-stiff and one-soft interlocking clamp is different from the clamp of elastic box of stiff true-triaxial testing system in that cushion blocks need to be completely disassembled.

In order to solve the technical problem, the clamp of elastic box of stiff true-triaxial testing system is characterized by comprising six pressing plates and eight plate springs.

The six pressing plates form a hexahedral empty box structure, each surface of the hexahedral empty box structure is provided by one pressing plate, a center of the hexahedral empty box structure is used as a coordinate origin, a spatial rectangular coordinate system is established in directions perpendicular to the six surfaces, the pressing plates on two opposite surfaces of an X-axis direction are a pressing plate X-a and a pressing plate X-b, the pressing plates on two opposite surfaces of a Y-axis direction are a pressing plate Y-a and a pressing plate Y-b, and the pressing plates on two opposite surfaces of a Z-axis direction are a pressing plate Z-a and a pressing plate Z-b.

One ends of the pressing plate X-a and the pressing plate X-b, away from the hexahedral empty box structure, are fixedly connected with two plate springs B along the Z-axis direction, and the other ends of the plate springs B are fixedly connected with the pressing plate Z-a and the pressing plate Z-b respectively; one ends of the pressing plate Y-b, away from the hexahedral empty box structure, is fixedly connected with the two plate springs B along the Z-axis direction, and the other ends of the plate springs B are fixedly connected with the pressing plate Z-a and the pressing plate Z-b respectively; and the pressing plate Y-a is fixedly connected with the two plate springs A along the X-axis direction, and the other ends of the plate springs A are fixedly connected with the pressing plate X-a and the pressing plate X-b respectively.

The plate springs A are L-shaped as a whole, and each plate spring A is provided with two screw holes at one end for mounting a spring jackscrew, and two screw holes at the other end as an embedded structure, so as to be used for being embedded into grooves of the pressing plate for fixation.

The one end of the plate springs A, with the two screw holes, is fixed on a jackscrew support plate on the pressing plate Y-a through the spring jackscrew, and by removing the spring jackscrew connecting the plate springs A and the pressing plate Y-a, so as to realize separation of the pressing plate Y-a from a flexible box.

The plate springs B are L-shaped as a whole, and each plate spring B is provided with three screw holes at one end, and the three screw holes are arranged in an inverted triangle. The parts of the two screw holes close to an outside are embedded into the grooves of the pressing plates, each plate spring B is provided with four screw holes at the other end, and the four screw holes are arranged in a square matrix. The parts of the two screw holes close to the outside are respectively embedded into the grooves of the pressing plates.

Three long screws are mounted on three screw holes close to inner sides of the plate springs B, the other ends of the long screws are pushed onto the corresponding pressing plates, and a cross fixing manner is used to limit a displacement of the pressing plates and adjust positions of the pressing plates at a center of a sample.

The plate springs are made of 65 Mn spring steel. The pressing plates are made of 40 Cr steel.

On the other hand, the invention further provides a displacement monitoring method for cuboid specimens by using the clamp of elastic box of stiff true-triaxial testing system, and the method comprises the following steps:

Step 1: mounting a rock sample to be tested in the elastic box clamp, wherein the process comprises:

Step 1.1: unscrewing the spring jackscrews on the jackscrew support plates on two sides of the pressing plate Y-a, so that the springs A are separated from the pressing plate Y-a, and at the same time, the pressing plate Y-a can be separated from the elastic box;

Step 1.2: sequentially loosening the screws for fixing the springs on the pressing plates on each surface in a small range until there is enough space which allows the rock sample to be put in;

Step 1.3: putting the rock sample with a copper foil on each surface into the elastic box clamp through a Y-a surface, and then fixing the pressing plate Y-a again to reserve pre-tightening space;

Step 1.4: sequentially tightening the screws on each surface in a small range, and in this process, paying attention to avoiding a position offset of the pressing plates and test pieces;

Step 1.5: performing fine tuning on the pressing plates in all directions until each pressing plate completely fixes the rock sample and keeps the rock sample at a center of the elastic box without the offset so as to complete sample mounting;

Step 2: mounting two sensor brackets at two ends of opposite corners of each pressing plate, wherein the pressing plates on different axes, namely, the sensor brackets on the symmetrical pressing plates are also symmetrical;

Step 3: fixing an adjusting bolt at one end of the sensor brackets on the pressing plate Z-a and the pressing plate Z-b which are symmetrical in the Z-axis direction, and fixing LVDT displacement sensors at the other end, wherein the adjusting bolt is connected with the LVDT displacement sensors, and the two LVDT displacement sensors are mounted in the Z-axis direction respectively at diagonal positions of the two pressing plates in the Z-axis direction;

Step 4: fixing the adjusting bolt at one end of the sensor brackets on the pressing plate X-a and the pressing plate X-b which are symmetrical in the X-axis direction, and fixing the LVDT displacement sensors at the other end, wherein the adjusting bolt is connected with the LVDT displacement sensors, and the two LVDT displacement sensors are mounted in the X-axis direction respectively at the diagonal positions of the two pressing plates in the X-axis direction;

Step 5: fixing the adjusting bolt at one end of the sensor brackets on the pressing plate Y-a and the pressing plate Y-b which are symmetrical in the Y-axis direction, and fixing the LVDT displacement sensors at the other end, wherein the adjusting bolt is connected with the LVDT displacement sensors, and the two LVDT displacement sensors are mounted in the Y-axis direction respectively at the diagonal positions of the two pressing plates in the Y-axis direction;

Step 6: mounting the elastic box clamp with the displacement sensors mounted on a true-triaxial stiff loading test device;

Step 7: enabling the true-triaxial stiff loading test device to load the elastic box clamp, and at the same time, monitoring a displacement change trend of the 6 LVDT displacement sensors in the X-axis direction, the Y-axis direction and the Z-axis direction.

The method adopting the technical scheme has the beneficial effects:

1. The elastic pressure box clamp provided by the invention only needs to remove one surface, slightly loosen cushion blocks around the rock sample, leaves a space for placing the sample, and the rock sample can be easily fixed in the elastic pressure box clamp by tightening the springs and is not liable to offset. The operation steps of mounting the rock sample are greatly simplified, and the mounting time is saved.

2. The springs connected with the pressing plates not only can ensure the stability of the clamp, but also cannot affect the stress state of other surfaces of the rock sample during a true-triaxial single surface unloading test of the rock sample, thereby ensuring the test accuracy.

3. The invention can realize rapid unloading of the principal stress by a traditional clamp, and can realize rock burst test researches.

In drawings, 1: plate spring A; 2: spring jackscrew; 3: jackscrew support plate; 4: pressing plate Y-a; 5: pressing plate Z-a; 6: LVDT displacement sensor; 7: sensor bracket A-a; 8: pressing plate X-a; 9: sensor bracket A-b; 10: adjusting bolt; 11: sample; 12: pressing plate Y-b; 13: hexagon socket head cap screws; 14: sensor bracket B-a; 15: plate spring B; 16: pressing plate X-b; 17: sensor bracket B-b; 18: pressing plate Z-b.

DETAILED DESCRIPTION OF THE PREFERRED EMBODIMENT

The embodiments of the invention will be further described in detail below in conjunction with the accompanying drawings and embodiments. The following embodiments are used to explain the invention, but are not used to limit the scope of the invention.

Figure 1:
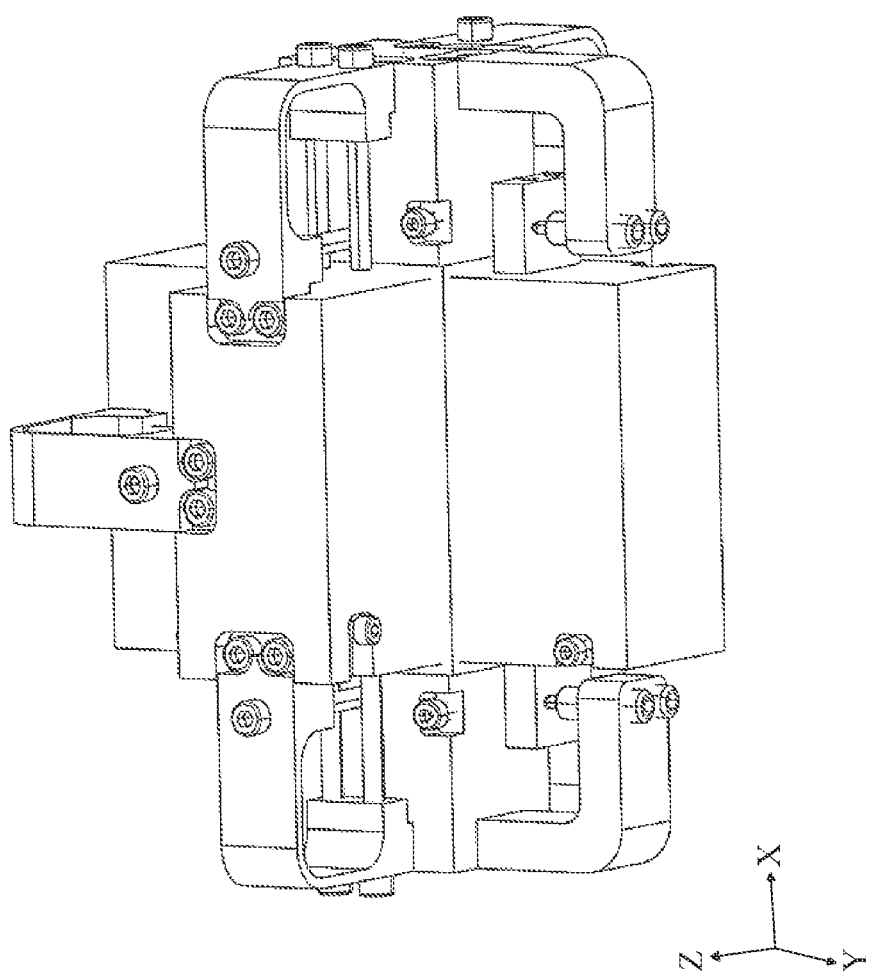
FIG. 1 is the overall structure diagram of a clamp of elastic box of stiff true-triaxial testing system in the embodiments.
Figure 2:
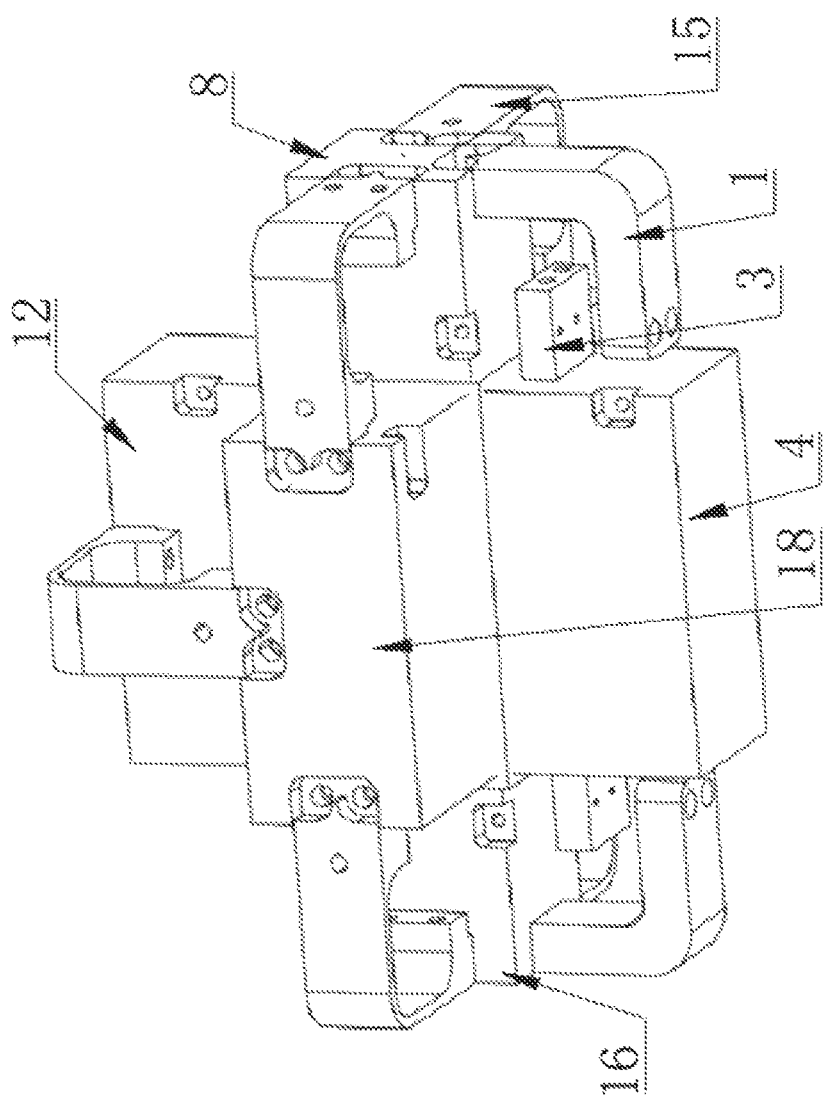
FIG. 2 is the position relationship diagram between pressing plates and the plate springs of the elastic box clamp in the embodiment of the invention.

The overall structure of the clamp of elastic box of stiff true-triaxial testing system disclosed by the embodiments is shown as FIG. 1 and comprises:

Six pressing plates and eight plate springs, wherein the position relationship between the pressing plates and the springs is shown as FIG. 2:

The six pressing plates form a hexahedral empty box structure, each surface of the hexahedral empty box structure is provided by one pressing plate, the center of the hexahedral empty box structure is used as a coordinate origin, a spatial rectangular coordinate system is established in directions perpendicular to the six surfaces, the pressing plates on two opposite surfaces of an X-axis direction are a pressing plate X-a 8 and a pressing plate X-b 16, the pressing plates on two opposite surfaces of a Y-axis direction are a pressing plate Y-a 4 and a pressing plate Y-b 12, and the pressing plates on two opposite surfaces of a Z-axis direction are a pressing plate Z-a 5 and a pressing plate Z-b 18;

One ends of the pressing plate X-a 8 and the pressing plate X-b 16, away from the hexahedral empty box structure, are fixedly connected with the two plate springs B 15 along the Z-axis direction, and the other ends of the plate springs B 15 are fixedly connected with the pressing plate Z-a 5 and the pressing plate Z-b 18 respectively; one ends of the pressing plate Y-b 12, away from the hexahedral empty box structure, is fixedly connected with the two plate springs B 15 along the Z-axis direction, and the other ends of the plate springs B 15 are fixedly connected with the pressing plate Z-a 5 and the pressing plate Z-b 18 respectively; and the pressing plate Y-a 4 is fixedly connected with the two plate springs A 1 along the X-axis direction, and the other ends of the plate springs A 1 are fixedly connected with the pressing plate X-a 8 and the pressing plate X-b 16 respectively.

Figure 3:
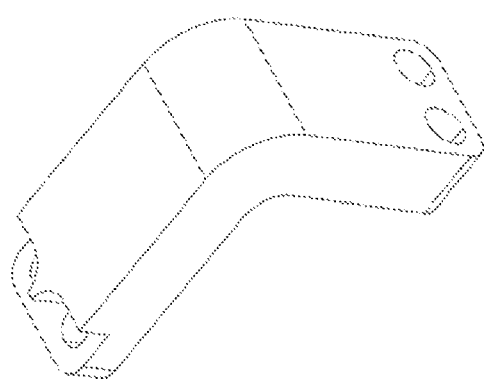
FIG. 3 is the structural diagram of plate springs A in the embodiment of the invention.

The plate springs A 1 are shown as FIG. 3 are L-shaped as a whole, and each plate spring A 1 is provided with two screw holes at one end for mounting a spring jackscrew 2, and two screw holes at the other end as an embedded structure, so as to be embedded into grooves of the pressing plate for fixation.

The one end of the plate springs A 1, with two screw holes, is fixed on a jackscrew support plate 3 on the pressing plate Y-a 4 through the spring jackscrew 2, and by removing the spring jackscrew 2 connecting the plate springs A 1 and the pressing plate Y-a 4, so as to realize separation of the pressing plate Y-a 4 from an elastic box.

Figure 4:
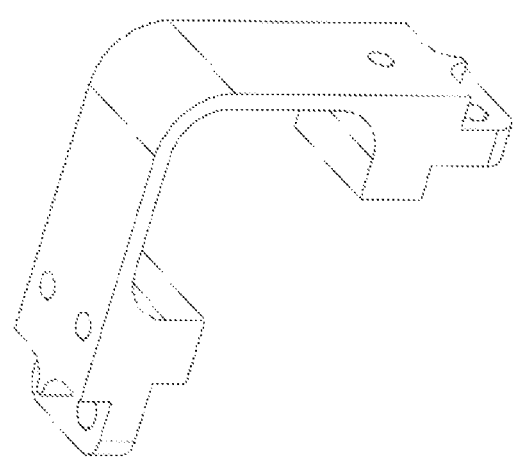
FIG. 4 is the structural diagram of plate springs B in the embodiment of the invention.

The plate springs B 15 as shown as FIG. 4 are L-shaped as a whole, and each plate spring B 15 is provided with three screw holes at one end, and the 3 screw holes are arranged in an inverted triangle. The parts of the two screw holes close to an outside are used to be embedded into the grooves of the pressing plates, each plate spring B is provided with 4 screw holes at the other end, the 4 screw holes are arranged in a square matrix, and the parts of the two screw holes close to the outside are respectively used to be embedded into the grooves of the pressing plates.

Three long screws 13 are mounted on three screw holes close to inner sides of the plate springs B 15, the other ends of the long screws 13 are pushed onto the corresponding pressing plates, and a cross fixing manner is used to limit a displacement of the pressing plates and adjust positions of the pressing plates at a center of a sample. The long screws 13 in the embodiment are the hexagon socket head cap screws.

The plate springs are made of 65 Mn spring steel. The pressing plates are made of 40 Cr steel.

According to the elastic box clamp disclosed by the embodiments of the invention, when the sample is mounted, only the springs A 1 at two ends of the pressing plate Y-a 4 need to be disassembled, then the pressing plate Y-a 4 can be completely taken down, the rock sample can be placed after the other pressing plates are slightly loosened, and after the sample is accurately placed, the pressing plate Y-a 4 is mounted back to the original position. The mounting can be completed by gradually tightening all of pressing plates.

On the other hand, the invention further provides a displacement monitoring method for cuboid specimens by using the clamp of elastic box of stiff true-triaxial testing system, and the method comprises the following steps.

Step 1: mounting a rock sample to be tested in the elastic box clamp, wherein the process comprises.

Step 1.1: unscrewing the spring jackscrews 2 on the jackscrew support plates 3 on two sides of the pressing plate Y-a 4, so that the springs A 1 are separated from the pressing plate Y-a 4, and at the same time, the pressing plate Y-a 4 can be separated from the elastic box.

Step 1.2: sequentially loosening hexagon socket head cap screws that fix the springs on the pressing plates on each surface in a small range until there is enough space to put the rock sample in.

Step 1.3: putting the rock sample with a copper foil on each surface into the elastic box clamp through a Y-a 4 surface, and then fixing the pressing plate Y-a 4 again to reserve pre-tightening space.

Step 1.4: sequentially tightening the hexagon socket head cap screws on each surface in a small range, and in this process, paying attention to avoiding a position offset of the pressing plates and test pieces due to overexertion.

Step 1.5: performing fine tuning on the pressing plates in all directions until each pressing plate completely fixes the rock sample and keeps the rock sample at the center of the elastic box without the offset so as to complete sample mounting.

According to the embodiments, a 50 mm×50 mm×100 mm rock sample is used as an example. Firstly, a hexagonal wrench is used to remove four spring jackscrews 2 fixed on the jackscrew support plate 3 from the pressing plate Y-a 4, and at this time, the pressing plate Y-a 4 is separated from the elastic pressure box; next, the screws of the pressing plates on each surface are sequentially loosened in a small range, the pressing plates in the Z direction of the elastic box are placed on a test bench, a tester shall face up to the surfaces of the pressing plate Y-a 4, the rock sample is slowly put into the elastic box clamp horizontally, then the clamp is rotated by 90 degrees to place the pressing plate Y-b 12 on the test bench, and the pressing plates in the X and Z directions are subjected to fine tuning, so that the rock sample can be adjusted to a central position; and finally, the pressing plate Y-a 4 is re-mounted to the original position, the elastic box clamp is sequentially rotated and the screws 13 are screwed up in a small range until the rock sample is kept at a center of the elastic box and clamped firmly to complete mounting.

Step 2: mounting two sensor brackets at two ends of opposite corners of each pressing plate, wherein the pressing plates on different axes, namely, the sensor brackets on the symmetrical pressing plates are also symmetrical.

Step 3: fixing an adjusting bolt 10 at one end of the sensor brackets on the pressing plate Z-a 5 and the pressing plate Z-b 18 which are symmetrical in the Z-axis direction, and fixing LVDT displacement sensors 6 at the other end, wherein the adjusting bolt 10 is connected with the displacement sensors 6, and the two LVDT displacement sensors 6 are mounted in the Z-axis direction respectively at diagonal positions of the two pressing plates Z-a 5 and Z-b 18 in the Z-axis direction.

Step 4: fixing the adjusting bolt 10 at one end of the sensor brackets on the pressing plate X-a 8 and the pressing plate X-b 16 which are symmetrical in the X-axis direction, and fixing the LVDT displacement sensors 6 at the other end, wherein the adjusting bolt 10 is connected with the LVDT displacement sensors 6, and the two LVDT displacement sensors 6 are mounted in the X-axis direction respectively at the diagonal position of the two pressing plates X-a 8 and X-b 16 in the X-axis direction.

Step 5: fixing the adjusting bolt 10 at one end of the sensor brackets on the pressing plate Y-a 4 and the pressing plate Y-b 12 which are symmetrical in the Y-axis direction, and fixing the LVDT displacement sensors 6 at the other end, wherein the adjusting bolt 10 is connected with the LVDT displacement sensors 6, the two LVDT displacement sensors 6 are mounted in the Y-axis direction respectively at the diagonal positions of the two pressing plates Y-a 4 and Y-b 12 in the Y-axis direction;

The sensor brackets and the pressing plates are fixed by the hexagon socket head cap screws, and the other end of each sensor bracket is an arc shaped clamp to fix the LVDT displacement sensors 6 with the hexagon socket head cap screws.

Figure 5:
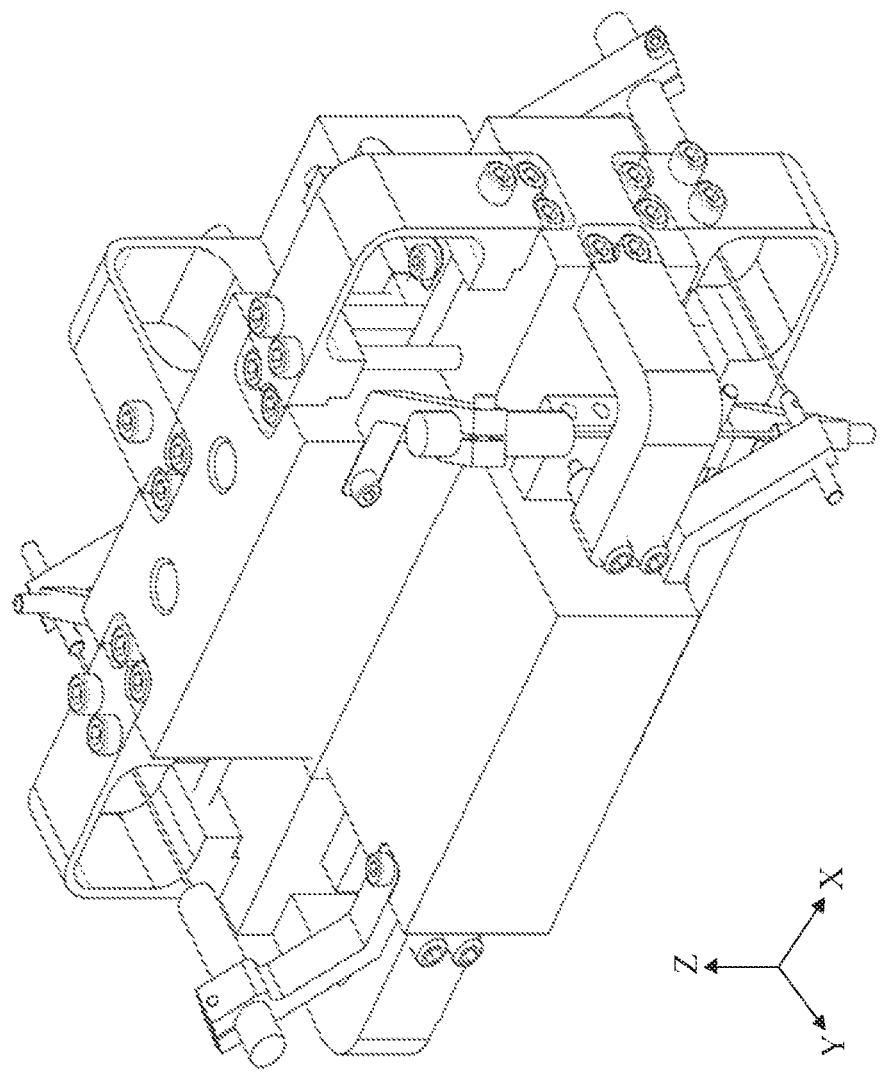
FIG. 5 is the overall structure diagram of the elastic box clamp with displacement sensors in the embodiment of the invention.
Figure 6:
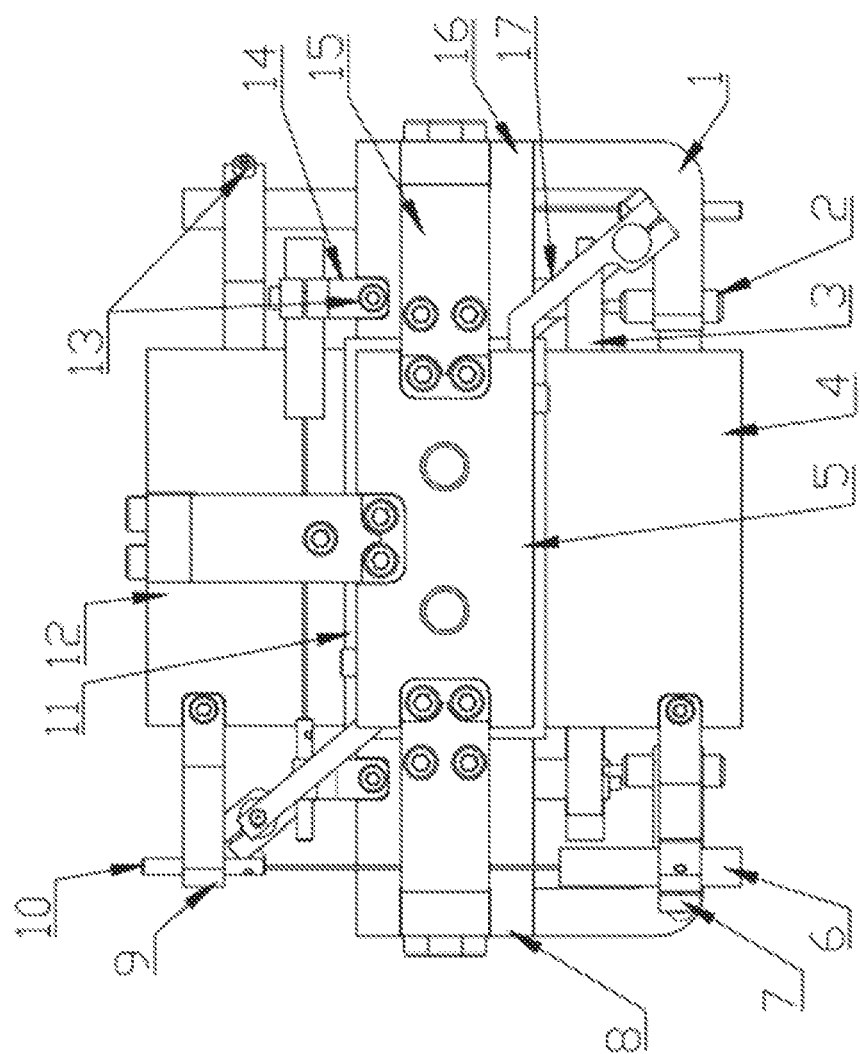
FIG. 6 is the top view of FIG. 5 in the embodiment of the invention.
Figure 7:
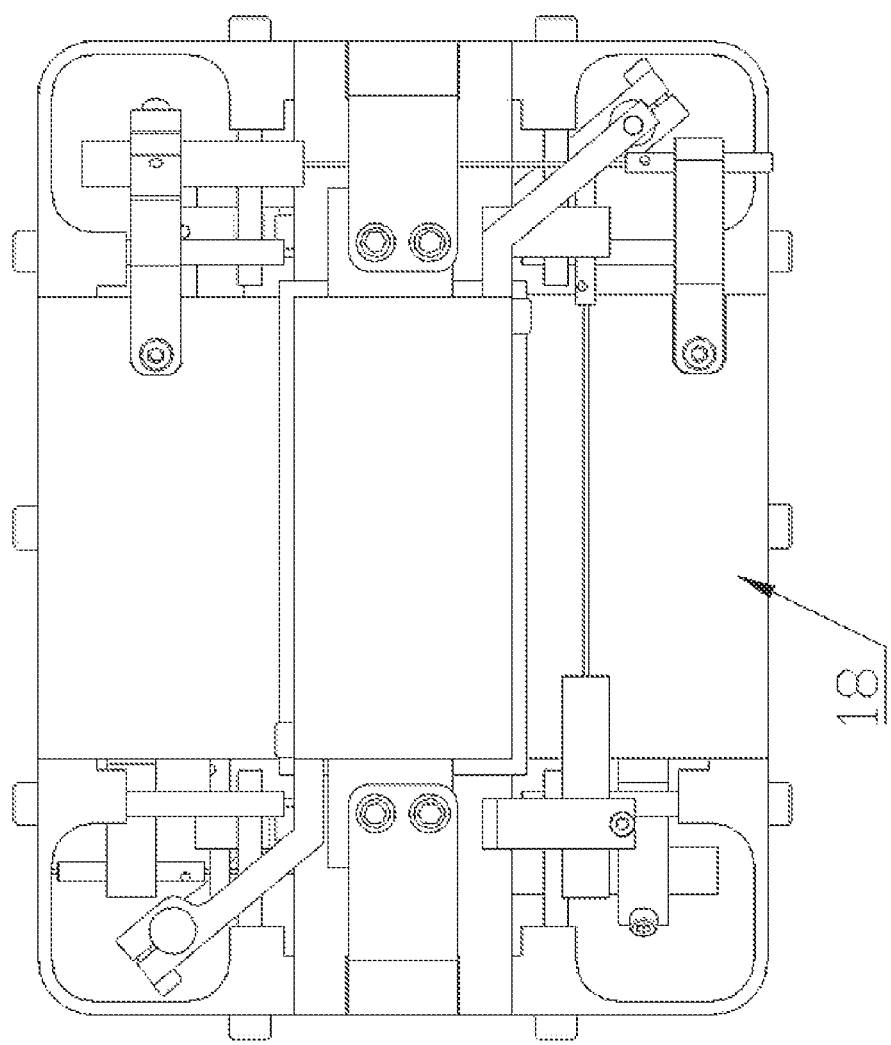
FIG. 7 is the front view of FIG. 5 in the embodiment of the invention.
Figure 8:
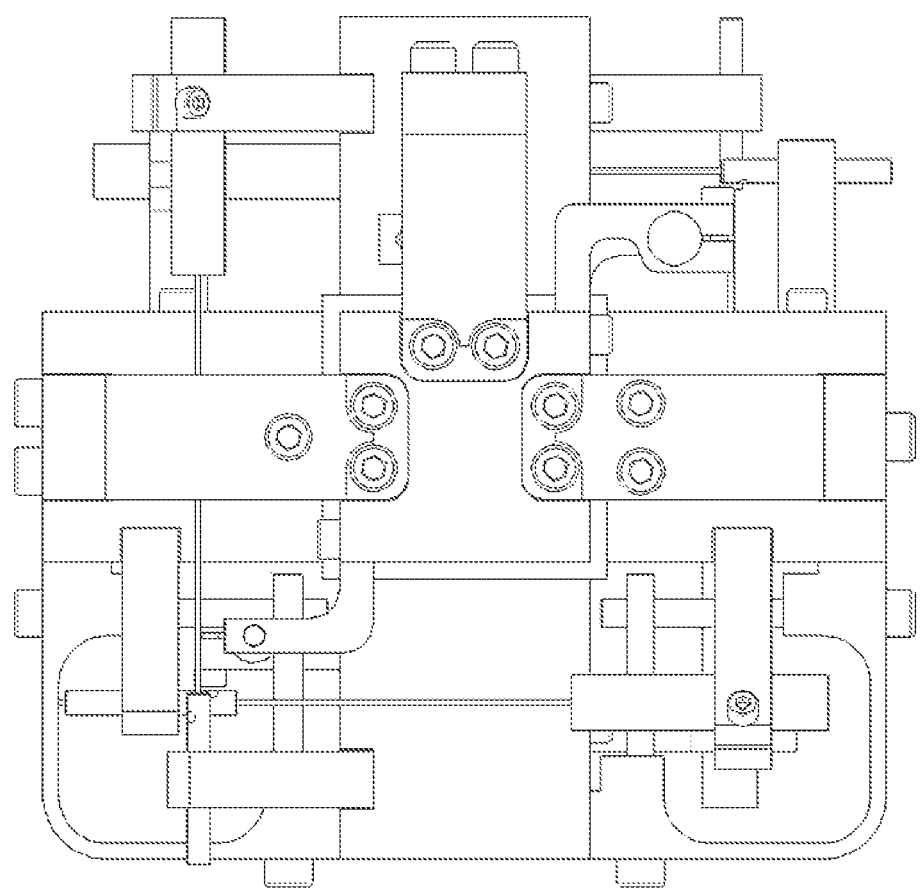
FIG. 8 is the left view of FIG. 5 in the embodiment of the invention.

In the embodiments, the overall structure of the elastic box clamp after mounting the LVDT displacement sensors 6 through the Steps 2 to 5 is shown in FIG. 5, and the top view, the front view and the left view are shown as FIG. 6, FIG. 7 and FIG. 8 respectively; and as can be seen from the figures, the two LVDT displacement sensors 6 are mounted on each axis.

Step 6: mounting the elastic box clamp with the displacement sensors 6 mounted on a true-triaxial stiff loading test device.

Step 7: enabling the true-triaxial stiff loading test device to load the elastic box clamp, and simultaneously monitoring a displacement change trend of the six LVDT displacement sensors 6 in the X-axis direction, the Y-axis direction and the Z-axis direction.

What is claimed is:

1. A clamp of elastic box of stiff true-triaxial testing system, comprising:
    six pressing plates and eight plate springs,
    wherein the six pressing plates form a hexahedral empty box structure, each surface of the hexahedral empty box structure is provided by one pressing plate, a center of the hexahedral empty box structure is used as a coordinate origin, a spatial rectangular coordinate system is established in directions perpendicular to the six surfaces, the pressing plates on two opposite surfaces of an X-axis direction are a pressing plate X-a and a pressing plate X-b, the pressing plates on two opposite surfaces of a Y-axis direction are a pressing plate Y-a and a pressing plate Y-b, and the pressing plates on two opposite surfaces of a Z-axis direction are a pressing plate Z-a and a pressing plate Z-b, and
    wherein one ends of the pressing plate X-a and the pressing plate X-b, away from the hexahedral empty box structure, are fixedly connected with two plate springs B along the Z-axis direction, and the other ends of the plate springs B are fixedly connected with the pressing plate Z-a and the pressing plate Z-b respectively; one end of the pressing plate Y-b, away from the hexahedral empty box structure, is fixedly connected with the two plate springs B along the Z-axis direction, and the other ends of the plate springs B are fixedly connected with the pressing plate Z-a and the pressing plate Z-b respectively; and the pressing plate Y-a is fixedly connected with two plate springs A along the X-axis direction, and the other ends of the plate springs A are fixedly connected with the pressing plate X-a and the pressing plates X-b respectively.

2. The elastic box clamp according to claim 1, wherein the plate springs A are L-shaped as a whole, each plate spring A is provided with two screw holes at one end for mounting a spring jackscrew and two screw holes at the other end as an embedded structure, so as to be embedded into grooves of the pressing plate for fixation.

3. The elastic box clamp according to claim 2, wherein the one end of the plate springs A, with the two screw holes, is fixed on a jackscrew support plate on the pressing plate Y-a through the spring jackscrew, and by removing the spring jackscrew connecting the plate springs A and the pressing plate Y-a, so as to realize separation of the pressing plate Y-a from an elastic box.

4. The elastic box clamp according to claim 1, wherein the plate springs B are L-shaped as a whole, each plate spring B is provided with three screw holes at one end, the three screw holes are arranged in an inverted triangle, the parts of the two screw holes close to an outside are embedded into grooves of the pressing plates, each plate spring B is provided with four screw holes at the other end, the four screw holes are arranged in a square matrix, and the parts of the two screw holes close to the outside are respectively embedded into the grooves of the pressing plates.

5. The elastic box clamp according to claim 1, wherein the plate springs are made of 65 Mn spring steel.

6. The elastic box clamp according to claim 1, wherein the pressing plates are made of 40 Cr steel.

7. The elastic box clamp according to claim 4, wherein three long screws are mounted on three screw holes close to inner sides of the plate springs B, the other ends of the long screws are pushed onto the corresponding pressing plates, and a cross fixing manner is used to limit a displacement of the pressing plates and adjust positions of the pressing plates at a center of a sample.

8. A displacement monitoring method for a rock sample by the elastic box clamp according to claim 1, comprising the following steps:
    Step 1: mounting the rock sample to be tested in the elastic box clamp;
    Step 2: mounting two sensor brackets at two ends of opposite corners of each pressing plate,
    wherein the pressing plates on different axes, namely, the sensor brackets on the symmetrical pressing plates, are also symmetrical;
    Step 3: fixing an adjusting bolt at one end of the sensor brackets on the pressing plate Z-a and the pressing plate Z-b which are symmetrical in the Z-axis direction, and fixing LVDT displacement sensors at the other end, wherein the adjusting bolt is connected with the LVDT displacement sensors, and the two LVDT displacement sensors are mounted in the Z-axis direction respectively at diagonal positions of the two pressing plates in the Z-axis direction;
    Step 4: fixing the adjusting bolt at one end of the sensor brackets on the pressing plate X-a and the pressing plate X-b which are symmetrical in the X-axis direction, and fixing the LVDT displacement sensors at the other end, wherein the adjusting bolt is connected with the LVDT displacement sensors, and the two LVDT displacement sensors are mounted in the X-axis direction respectively at the diagonal position of the two pressing plates in the X-axis direction;
    Step 5: fixing the adjusting bolt at one end of the sensor brackets on the pressing plate Y-a and the pressing plate Y-b which are symmetrical in the Y-axis direction, and fixing the LVDT displacement sensors at the other end, wherein the adjusting bolt is connected with the LVDT displacement sensors, and the two LVDT displacement sensors are mounted in the Y-axis direction respectively at the diagonal position of the two pressing plates in the Y-axis direction;

Step 6: mounting the elastic box clamp with the displacement sensors mounted on a true-triaxial stiff loading test device; and Step 7: enabling the true-triaxial stiff loading test device to load the elastic box clamp, and at the same time, monitoring a displacement change trend of the six LVDT displacement sensors in the X-axis direction, the Y-axis direction and the Z-axis direction.

9. The displacement monitoring method according to claim 8, wherein the process of the Step 1 comprises:

Step 1.1: unscrewing the spring jackscrews on the jackscrew support plates on two sides of the pressing plate Y-a, so that the springs A are separated from the pressing plate Y-a, and at the same time, the pressing plate Y-a can be separated from the elastic box;

Step 1.2: sequentially loosening the screws for fixing the springs on the pressing plates on each surface in a small range until there is enough space to put the rock sample in;

Step 1.3: putting the rock sample with a copper foil on each surface into the elastic box clamp through a Y-a surface, and then fixing the pressing plate Y-a again to reserve pre-tightening space;

Step 1.4: sequentially tightening the screws on each surface in a small range, and in this process, paying attention to avoiding a position offset of the pressing plates and test pieces; and Step 1.5: performing fine tuning on the pressing plates in all directions until each pressing plate completely fixes the rock sample and keeps the rock sample at a center of the elastic box without the offset so as to complete sample mounting.

\* \* \* \* \*